United States Patent [19]

Schneiderman

[11] 4,051,855
[45] Oct. 4, 1977

[54] ELECTROSURGICAL UNIT

[75] Inventor: Max Schneiderman, Clifton, N.J.

[73] Assignee: IPCO Hospital Supply Corporation, Whaledent International Division, New York, N.Y.

[21] Appl. No.: 655,887

[22] Filed: Feb. 6, 1976

[51] Int. Cl.² .................... A61B 17/36; A61N 3/00
[52] U.S. Cl. .................... 128/303.14; 128/303.17; 128/422; 336/69; 336/208
[58] Field of Search .................... 128/303.14, 303.17, 128/303.13, 303.18, 422; 336/69, 170, 208

[56] References Cited

U.S. PATENT DOCUMENTS

| 1,605,302 | 11/1926 | True | 336/170 X |
|---|---|---|---|
| 1,868,155 | 7/1932 | Wheeler | 336/170 X |
| 1,945,867 | 2/1934 | Rawls | 128/303.14 |
| 3,601,126 | 8/1971 | Estes | 128/303.14 |
| 3,675,655 | 7/1972 | Sittner | 128/303.14 |
| 3,804,096 | 4/1974 | Gonser | 128/303.14 |
| 3,834,392 | 9/1974 | Lampman et al. | 128/303.13 |
| 3,885,569 | 5/1975 | Judson | 128/303.14 |
| 3,952,748 | 4/1976 | Kaliher et al. | 128/303.14 |
| 3,964,487 | 6/1976 | Judson | 128/303.14 |

FOREIGN PATENT DOCUMENTS

| 51,638 | 5/1936 | Denmark | 128/422 |
|---|---|---|---|
| 2,044,078 | 5/1972 | Germany | 128/303.14 |

Primary Examiner—Robert W. Michell
Assistant Examiner—Lee S. Cohen
Attorney, Agent, or Firm—Friedman, Goodman & Teitelbaum

[57] ABSTRACT

An electrosurgical unit for use in tissue cutting or coagulation procedures. A vacuum tube oscillator operating in push-pull relationship generates RF oscillations which are extracted across a balanced coil transformer, the secondary of which is ungrounded. Forceps are provided to be connected across the output of the transformer for producing an isolated voltage for use in sealing off bleeding blood vessels. A handpiece is also provided for connection across the transformer output for selectively producing a cutting voltage or a coagulation voltage. An intensity control circuit is capable of connection in the power supply to control the output voltage. A pulse modulation unit is capable of being connected at the input of the oscillator to control the "on" time of the oscillator. A switching circuit operates to interconnect the intensity control to the power supply when the cutting probe is being utilized for cutting procedures, and connects the pulse modulation unit to the oscillator when the coagulation signal is being provided across either the forceps or the handpiece. An indifferent plate, also known as a dispersion electrode, is utilized together with the handpiece for cutting procedures. The indifferent plate is completely isolated from ground to prevent shocks and burns occurring on the patient at inadvertent ground points.

22 Claims, 14 Drawing Figures

ELECTROSURGICAL UNIT

BACKGROUND OF THE INVENTION

This invention relates to electrosurgical devices and more particularly to an improved electrosurgical unit capable of providing an unmodulated signal for cutting tissue and a modulated signal for coagulation.

High frequency oscillations have been utilized for various electrotherapeutic purposes. Some devices utilize the electrostatic field produced by a high frequency oscillator for surgery, coagulation, or sterilization of utensils. For example, U.S. Pat. No. 1,945,867 teaches the creation of such high frequency oscillatory electrostatic field which is utilized for electrotherapeutic purposes. More recently, use has been made of the high frequency electrical current produced. Electrosurgery has been carried out based upon the ability to localize and control the heating effect from such high frequency electrical current. Such electric current is localized at a sharp point, usually by means of a pointed electrode, to create a high current density which provides the intense localized power needed for tissue effect. A return electrode, usually a large plate positioned under the patient, returns the current back to the electrosurgical unit. By having a rather large return plate, the current density is dispersed, causing a low current density at the contact with the return plate.

It has been found that tissue cutting can be produced by utilizing an undamped signal, while coagulation can be achieved by utilizing a damped frequency signal. Spark gap oscillators generally produce damped waveforms while vacuum tube oscillators produce undamped waveforms. As a result, many electrosurgical devices providing both tissue cutting and tissue coagulation outputs will utilize a spark gap generated waveform for coagulation, and a vacuum tube oscillator for tissue cutting. Typical of such unit is described in U.S. Pat. No. 3,058,470. Other electrosurgical units will rather utilize a single oscillator which alternates between damped and undamped signals. For example, U.S. Pat. No. 3,261,358 provides such alternating output. Also, U.S. Pat. No. 3,478,744 provides a modulated output which finds use for both cutting and coagulation. While vacuum tube oscillators are generally preferred, many units do not use them because they are usually bulky and heavy and require a long amount of warm up time during the turn-on periods.

In general, all electrosurgical units provide a return electrode, frequently called the dispersion electrode, the indifferent plate, or the butt plate. Most such prior art units extract the oscillator output across an output transformer which has either one end, or a midpoint grounded, whereby the return plate operates as a ground plate. The use of this type of grounded output unit has created many surgical problems and numerous patient injuries. The main purpose of the return plate is to disperse the current and create a low current density contact between the patient and the return path. If the patient accidentally touches a piece of grounded metal, such as the operating table, there will occur a grounded return path at that point of contact. However, the contact point will be very small which will result in a high density current causing a burn at the contact point. Even if precautions are taken to prevent contact between the patient and the operating table, it is practically impossible to avoid complete contact, because of conductive paths provided by the spillage of blood, or saline solutions. Additionally, there generally exists capacitive paths between the patient and ground which can also cause return paths to ground with possible burns at the points of close contact between the patient and ground. In recent times where numerous monitoring units, such as EKGs, ECGs, etc., are connected to the patient during a surgical operation, the point of contact between such peripheral electrical equipment and the patient also causes the possibility of high current densities flowing at such points of contacts which may also cause burns as the current flows through the equipment to ground. A further hazard can result if the return cable to the electrosurgical unit breaks or if the return plate accidentally becomes disconnected. The current will then seek alternate ground paths through the patient. Such alternate contacts will frequently be over a very small area causing severe patient burns.

A solution has been presented to provide an isolated output unit where the return plate is ungrounded and is in fact isolated from ground. In this way, the current will not seek ground contacts as return paths since the electrosurgical unit is isolated from ground. However, it has heretofore not been possible to obtain a very good isolated output and frequently, stray pathways to ground within the unit defeated the attempted isolation.

Since the accidental disconnection of the return plate can cause burns in the patient as well as other hazardous conditions, many prior art units contain sensory warning devices to give an indication when such disconnection occurs or when the cable is broken. However, in most prior art units, even though the return plate is disconnected, the probe will still provide the high current density and continue cutting tissue, thereby continuing the possibility of burns.

Prior art electrosurgical units have also presented other problems. In many cases it is desired to provide alternately either a coagulation signal or a cutting signal. Some units have provided two separate output probes, one for coagulation and one for cutting. However, frequently, both units are simultaneously activated so that while one of the probes is being used, someone may accidentally pick up the other probe and burn their hand. Some electrosurgical units only provide a single probe for alternately supplying a cutting or a coagulating output. With these units, however, when the surgeon is utilizing the single probe, it is not possible for an assistant to provide coagulation support to the surgeon.

Another difficulty with prior art electrosurgical units is in connection with the magnitude of the coagulation or cutting output voltage. It is necessary to control the magnitude of these outputs depending upon the depth of cut, the impedance provided by the patient, and various other factors. Most units do provide some type of intensity control. However, the intensity control set for a cutting procedure may not be suitable for a coagulation procedure. As a result, it is necessary for the surgeon to reset the unit as he alternates between coagulating and cutting.

Furthermore, in providing the modulated output for coagulation purposes, most electrosurgical units provide a single level of modulation, and usually use a standard 60 cycle per second output. However, it has been found that the patient acts as a rectifier for such 60 cycle modulation and muscle spasm will result during the coagulation procedure.

Still a further problem with many eklectrosurgical units is that the switching between the coagulation and the cutting takes place at a high voltage. As a result, the possiblity of sparking exists and when using explosive chemicals there is the dangerous possiblity of an explosion occurring in the operating room.

SUMMARY OF THE INVENTION

It is accordingly an object of the present invention to provide an electrosurgical unit which avoids the aforementioned problems of prior art devices.

It is another object of the present invention to provide an electrosurgical unit with a highly isolated output.

Yet a further object of the present invention is to provide an electrosurgical unit which utilizes two vacuum tubes in push-pull arrangement, in conjunction with a balanced transformer coil, to thereby produce a high isolated output.

Still a further object of the present invention is to provide an electrical surgical unit which provides a forceps for sealing blood vessels and a handpiece for cutting.

Another object of the present invention is to provide an electrosurgical unit which utilizes a handpiece to selectively provide either a coagulation or a cutting output voltage.

Still another object of the present invention is to provide an electrosurgical unit which provides independent control for the level of the cutting voltage and the level of the coagulation voltage.

A further object of the present invention is to provide an electrosurgical unit which includes a standby circuit for providing low standby power to heat the filaments of the oscillator vacuum tubes thereby minimizing the warm up period.

Still another object of the present invention is to provide an electrosurgical unit which includes an interlock coupled to the return plate for stopping the cutting output and providing a warning signal when the return plate is disconnected.

Still a further object of the present invention is to provide an electrosurgical unit which contains a standby switch and an operating switch and which includes a preventive circuit to prevent simultaneous activation of both these switches.

Another object of the present invention is to provide an electrosurgical unit which contains output indicators for coagulation, cutting, standby, and operating conditions.

Yet a further object of the present invention is to provide an electrosurgical unit which utilizes an improved transformer unit which prevents unbalance and reduces capacitive leakage to ground.

Still another object of the present invention is to provide an electrosurgical unit which utilizes low voltage switching to prevent the possibility of explosions.

Briefly, the invention provides an electrosurgical unit which includes a vacuum tube oscillator means for providing an ungrounded output of a given frequency. A power supply means supplies the oscillator with a voltage. A coagulation output means is available for coupling to the oscillator means and providing a coagulation voltage for use in coagulation procedures. A cutting output means is also available for coupling to the oscillator means and providing a cutting voltage for use in cutting procedures. A switching circuit means can selectively connect the coagulation output means or the cutting output means to the oscillator means. An intensity control means is also available for coupling to the power supply and varying the voltage provided to the oscillator means. A modulation means is also available for coupling to the oscillator means and providing intermittent operation of the oscillator means. The switching means interconnects the intensity control means to the power supply means only when the cutting output means is connected to the oscillator means, and interconnects the modulation means to the oscillator means only when the coagulation output means is connected to the oscillator means.

The cutting output means further includes a handpiece unit for applying the cutting voltage as a high density RF voltage and a return plate for returning the current to the oscillator means. Neither the handpiece unit nor the return plate are grounded, and both are highly isolated from ground.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawings, like reference characters designate like parts.

DESCRIPTION OF THE PREFERRED EMBODIMENT

Electrosurgical units generally contain an RF oscillator which provides a high frequency output electrical current which is extracted across an output transformer. The current is applied to the patient from an electrode in a handpice unit and returns from a wide area return plate, hereinafter referred to as the indifferent plate.

Figure 1:
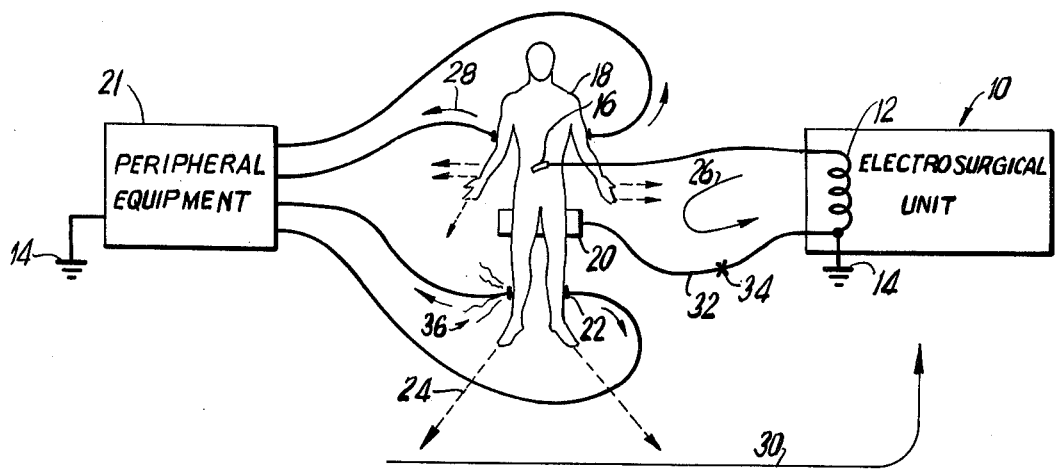
FIG. 1 is a schematic drawing of a grounded output electrosurgical unit connected to a patient.
Figure 2:
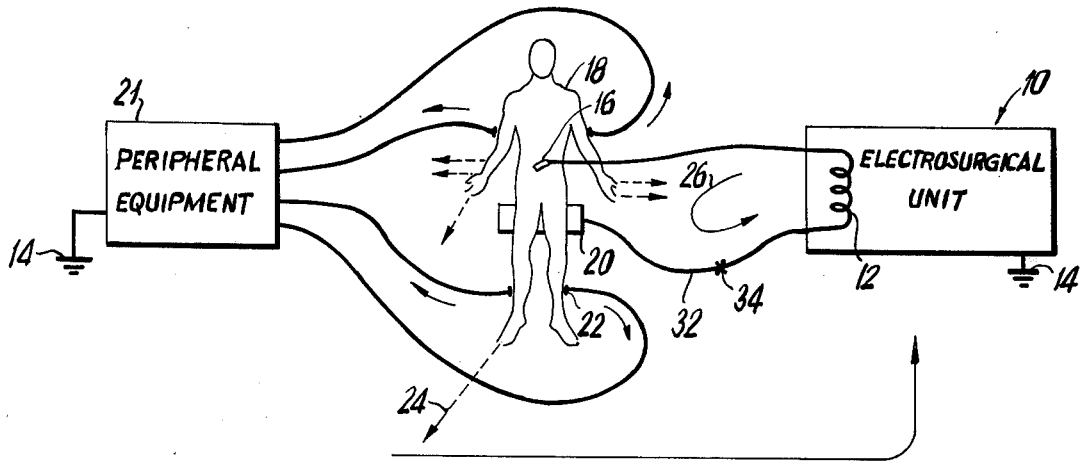
FIG. 2 is a schematic drawing of an isolated output electrosurgical unit connected to a patient.

Referring now to FIGS. 1 and 2 there will be compared the non-isolated or grounded output unit, shown in FIG. 1, with the isolated output unit, shown in FIG. 2. In FIG. 1, the electrosurgical unit, shown generally at 10 indicates an output transformer 12 having one end thereof grounded at 14. The high frequency output current is applied by means of a handpiece electrode 16 to the patient 18. The current path returns through the indifferent plate 20, generally placed under a wide area of the patient such as the buttocks. It will therefore be appreciated that the return plate is in fact grounded. The indifferent plate is generally made large to permit a broad area of contact with the patient thereby providing a low current density path for the return current. In fact, the only difference between the handpiece 16 and the plate 20 is that the handpiece provides a high density current which thereby causes the burning or cutting of the tissue, while the low density plate 20 will not cause any such burning or cutting.

Frequently there are connected additional peripheral electrical equipment 21 such as monitoring units, EKG units, etc. These equipment units are grounded and are connected to the patient by means of contacts, for example, contacts 22. As a result these contacts also provide a path leading to ground. Additionally, there exists capacitive paths, shown by the dotted lines 24, between the patient and ground. As a result, the main current path from the electrosurgical unit will pass through the probe 16 and return through the indifferent plate 20, as shown by path 26. However, additional current paths 28 will also exist through the contacts 22 to the peripheral equipment 21, as well as current paths 30 through the capacitive coupling to ground. At any of these additional current paths a burn could result if there is a small enough area of contact. Such small are of contact would duplicate the probe electrode 16 and cause a high density RF current to flow which will burn, and may cut the tissue.

An even more serious problem can occur if the return cable 32 were to be severed, as for example at point 34. In this case there no longer exists the wide area of the indifferent plate to provide a low density return path. The current will therefore seek the alternate paths to return to ground and will cause severe burns, as shown at contact 36.

In the isolated system, shown in FIG. 2, the output transformer 12 is not grounded and is therefore isolated from ground. As a result, neither the handpiece 16 nor the indifferent plate 20 is grounded and there only exists the single current path 26 flowing from the handpiece, througe the patient, the back to the electrosurgical unit through the indifferent plate 20. While the electrosurgical unit itself may be grounded at 14, the output transformer is isolated from ground and prevents any current flow path to ground. As a result, even though peripheral equipment 21 may be connected to the patient through contacts 22, and although capacitive paths 24 may exist to ground, these do not provide any current flow path back to the electrosurgical unit. Furthermore, even if the return cable 32 should be severed at 34, no burns would occur at any of the contacts 22, and in fact, no further current would flow from the electrosurgical unit 10 to the handpiece 16.

While in theory the isolated output units provide beneficial results, in practice it has heretofore not been possible to achieve such perfect isolation and even isolated output units have caused burns, and other problems to both patients and peripheral equipment.

The present invention is of the isolated type system, heretofore described, but is capable of providing an exceedingly high isolation from ground due to the use of an improved RF generating circuit in conjunction with low capacitance interconnecting cables and an improved design for the output coil. Although prior art electrosurgical units have utilized vacuum tubes, the trend has been to eliminate such use because of the bulky size involved as well as the long delays which occur during warm-up of the filaments when the vacuum tubes are turned on. These problems have been avoided in the present invention by the unique design of the electrosurgical unit to be described in conjunction with FIG. 3.

The RF electrical current is provided by means of the oscillator 40 which includes two vacuum tubes 42, 44 connected in push-pull relationship. The cathodes 46, 48 of the tubes are interconnected along line 50. A first control grid 52, 54 of each tube are interconnected through respective resistors 56, 58 to opposite ends G, G' of the grid coil 60 of the transformer to be hereinafter described. The centerpoint Gc of the grid coil is connected through resistor 62 to ground 64. The second grid 66, 68 of each tube are interconnected along line 70 and coupled through resistor 72 to the power supply 74 to be hereinafter described. Capacitor 76 connected to ground, filters the high voltage supplied to the tubes.

A third control grid 78, 80 of each tube, is respectively connected to the filaments 46, 48 of the tubes through the capacitors 82, 84. The plates of the tube 86, 88 are interconnected to the end points P, P' of the plate coil 90 of the transformer. The centerpoint Pc of the plate coil is also connected to the main power supply 74.

The output coil 92 of the transformer has its ends 0, 0' connected across a tuning capacitor 94 and connects to the centerpoints of switches 96, 98 of the switching circuit 100. Switches 96, 98 are normally in their cutting position $a$ which respectfully interconnects to the cutter handpiece shown generally at 102, and the indifferent plate or dispersion electrode shown generally at 104. When the switches 96, 98 are connected to their positions $b$, they interconnect to the coagulation forceps, shown generally at 106.

The forceps 106 provide the means for sealing blood vessels and includes the two arms 108, 110 connected to the main unit by means of a plug and jack 112. The outer shield 114 of the forceps is also connected through the plug and jack to a ground through line 116. When the two ends of the forceps are brought together, an integral switch 118 is closed contacting onto point 120 which is connected to ground 116 through resistor 122. Closing of the switch 118, energizes the relay coil 124 whose other end is connected to the +V supply, which is a low voltage supply.

The cutter handpiece 102 includes an electrode 126 coupled through the plug and jack arrangement 128 to the position $a$ of switch 98. The shield 130 of the probe electrode is coupled to the shield 132 of the indifferent plate 134. A coag/cut switch 136 is contained on the probe so that the user can provide both a cutting signal and a coagulation signal by using the same probe. When placed on its coag position, it interconnects point 138 with point 140. Switch 142 is available to connect ground 144 to point 138 or point 140. When switch 136 is placed in its cut position, it connects point 138 to point 146.

A foot pedal, shown generally at 150, operates in parallel with the switch 136 whereby the user can either manipulate the hand switch 136 to obtain the coag or cutting signal from the handpiece 102 or can utilize the foot pedal to obtain the same results. The foot pedal includes two separate switches 152 and 154. When desiring a coagulation output, switch 152 is moved from its normal position C to position $d$ which interconnects point 138 with point 140, similar to the action of switch 136. When a cutting signal is desired, switch 154 is moved from its normal position $f$ to position $e$ which interconnects point 138 to point 146, similar to the action of switch 136. The foot pedal 150 is connected to the main unit through the plug and jack arrangement 156. If both foot pedal switches are inadvertently activated at the same time, only the coagulate function is provided.

The indifferent plate 134 is connected through a plug and jack arrangement 158 to position a of switch 96. An interlock circuit 160 is also connected to the plug and jack to provide a visual indication when the plug and jack arrangement 158 has been opened. A low voltage supply +V passes through resistor 162 and is normally shorted to ground 166 though the shorting wire 164 on the plug side of the plug and jack arrangement 158. However, when the plug has been displaced from the jack, the current will pass through the light emitting diode 168 to provide a visual indication of the disconnection. At the same time, when the indifferent plate 134 has been removed from the circuit, no voltage will pass through the probe unit 102 since both the probe and the indifferent plate are connected to opposite ends of the output coil 92 and no return path to the unit will be then provided.

A multivibrator unit, shown generally at 170 is adapted to be coupled to the input of the oscillator unit 40 to effectively pulse modulate the operation of the oscillator. The multivibrator 170 includes transistors 172 and 174 whose emitters are coupled together along line 176 and whose collectors are respectively connected to resistors 178 and 180. The base of transistor 172 is interconnected to the collector of transistor 174 through capacitor 182 while the base of transistor 174 is connected to the collector of transistor 172 through capacitor 184. The bases of the two transistors are interconnected through the fixed base resistors 186 and 188 and through the variable resistor 190 which is controlled by means of the variable control 192 connected at the end of resistors 178 and 180 which is also connected to the +V supply.

By means of the variable control 192, it is possible to control the duty cycle of the multivibrator and thereby control the pulse width of the output pulses produced.

One of the output pulses of the multivibrator 170 is applied to the amplifier switch circuit 194. This circuit includes a first transistor 196 having its emitter coupled to the +V supply and its collector coupled through a voltage divider comprising resistors 198, 200 to the base of a grounded emitter transistor 202. A diode 204 is connected across the collector-emitter path of transistor 196. The base of transistor 196 is connected through the resistor 206 to one of the outputs of the multivibrator 170 and specifically to the collector of transistor 172. It is also coupled to point 146 and also connected through capacitor 208 to ground. The collector of transistor 202 is connected to line 50 of the oscillator unit and the emitter of transistor 202 is grounded.

When the multivibrator 170 is operating, one polarity of the output pulses will be applied through the transistor 196 and inverted by the transistor 202 to control the oscillator 40. Each time that pulse appears, the oscillator will be operative. By means of the coag level control 192, the on time of the oscillator can be controlled. At the same time, when the point 146 is grounded by placing the switch 136 or the foot pedal 150 in the cut position, the transistor 196 will cause the oscillator to be continuously operative.

Power is supplied to the unit through the main power supply 74 which is interconnected to an AC source 208. The current passes through a circuit breaker 210 and through the series of cross connected switches 212 to the transformer 214. The output of transformer 214 is rectified by means of the rectifier 216 and filtered by the filter 218 to provide a high voltage output at line 220. This high voltage output is fed through the switch 222, which is normally in its open position g. When the operating switch 224 is moved upward to its run position, switch 222 is caused to move to position h which interconnects the high voltage to the point Pc of the plate transformer coil 90, as well as to the screen grids 66 and 68 of the tubes 42 and 44 of the oscillator.

The primary of the transformer 214 is connected to a variac coil 226. The variac can be controlled by means of the control arm 228. The variac is interconnected to the primary by means of the switch 230 being in position i. When moved to position j, the variac is removed from the circuit. In position j, the maximum output voltage is provided from the power supply, while in position i, the control arm 228 can vary the output from a low value up to its maximum value.

An auxillary and filament supply circuit 232 is provided for forming the filament current to heat the vacuum tubes as well as to provide the low voltage supply for operating the tubes and transistors. The auxillary and filament supply 232 is connected to the main power lines by means of the transformer 234. One end of the secondary of the transformer 234 is connected to point 236 and the other end is connected to point 238. The center tap is connected to point 240. A standby indicator bulb 242 has one end connected to resistor 246, and its other end connected to point 248. A run indicator bulb 244 is connected between resistor 246 and point 250. Switches 252 and 254 are operated by means of the standby switch 256. The filament output is taken across the end of switch 252 on the one hand, and the point 236 on the other hand.

When the switch 256 is upward in its standby position, point 236 will be connected to one end of the transformer 234 and, with switch 252 in its upward position on point 240, the other end of the filament output will be connected to the mid point of the transformer 234. In this way, only half of the output of the transformer 234 will be applied to the filament. At the same time, switch 254 will be upward on position 248 which interconnects the standby bulb 242 directly across the entire output of the transformer 234 so that the entire output voltage will be available to energize the standby bulb 242.

When the standby position is lowered, during full operation of the unit, switch 252 will be in its lower position contacting 238 whereby the entire output voltage of the transformer 234 will be available to heat the filament. This voltage will be twice as much as the standby voltage and will be sufficient to fully operate the vacuum tubes of the oscillator. At the same time, switch 254 will also be in its lower position contacting point 250 which will place the entire output voltage of the transformer 234 across the run bulb 244 to energize it.

In the above described manner, during standby operation, a low voltage will be supplied to the filament to permit it to remain in a slightly heated position so that when full operation of the unit is desired, a reduced amount of time will be needed to fully heat up the unit.

Rectifier 257 is connected across the filament output, and filter 258 filters the output from the rectifier. The filtered output provides the low voltage supply +V which is utilized to energize the transistors and relay coils of the circuit.

Standby switch 256 and operating switch 224 can both be activated independently. Since no mechanical lockout is provided between the two switches, the circuit 212 is arranged to prevent simultaneous operation of both these switches. The circuit includes switches 260 and 260' on the one hand, which operate in opposition to switches 262 and 262' on the other hand. The wires interconnecting switches 260 and 262, as well as the wires interconnecting 260' and 262' are crossed. In this manner, current will be provided to the transformers 214 and 234 only when the standby switch 256 and the operating switch 224 are opposite to each other. Specifically, if the standby switch is in its upward position, indicating a standby condition, the operating switch 224 must be in its lower position in order for current to be supplied. At the same time, when the operating switch 224 is placed upward, indicating a run position, the standby switch 256 must be in its lower position in order for current to flow.

An indicating circuit 264 is available for indicating whether the circuit is operting to supply a coagulation output or a cutting output. The indicating circuit is connected through a diode 266 to the line 50 of the oscillator unit, and includes a light emitting diode 268 for indicating when the cutting output is being supplied, and a light emitting diode 270 to indicate when the coagulation output is being supplied. The two light emitting diodes are connected to ground on the one hand through resistor 272 and on the other hand to opposite contacts of a switch 274. The switch 274 is connected through resistor 276 to the low voltage supply +V.

The switch 274 is operated by means of the relay coil 280 connected in the collector circuit of the transistor 278 whose emitter is connected to the low voltage supply +V. The base of transistor 278 is connected through the base resistor 282 and a choke 284 to the position 140. The capacitor 285 filters the base of transistor 278 to ground.

Figure 3:
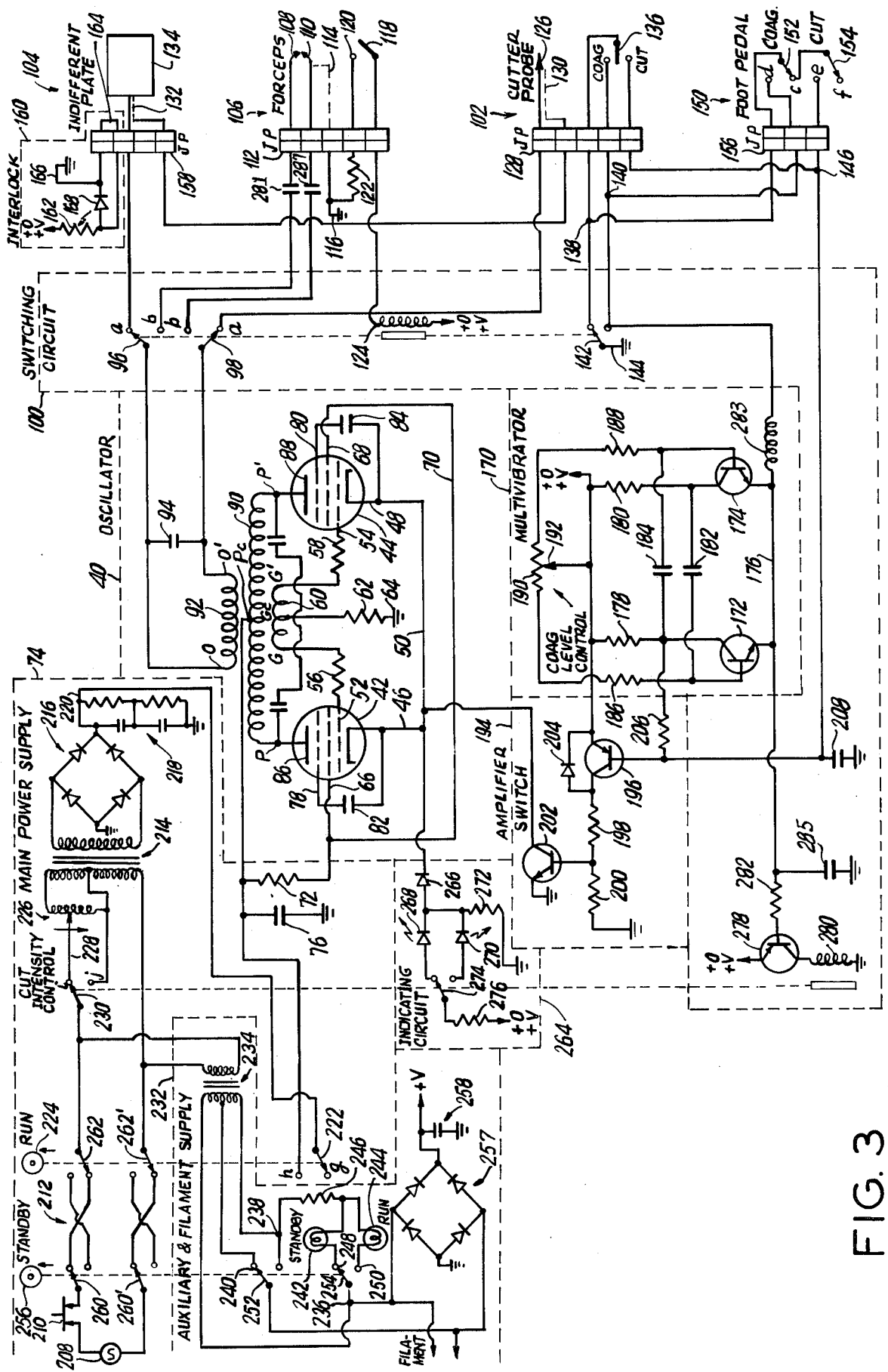
FIG. 3 is a circuit drawing of an electrosurgical unit, in accordance with the present invention.
Figure 4A:
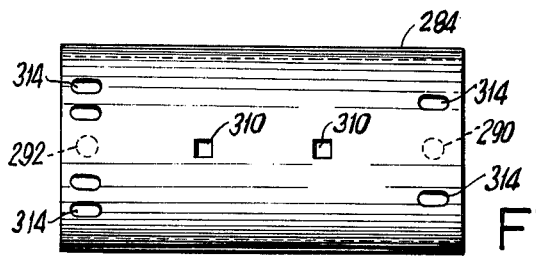
FIGS. 4A, 4B and 4C show side elevational views of the sections of the coil assembly, in accordance with the present invention.
Figure 5A:
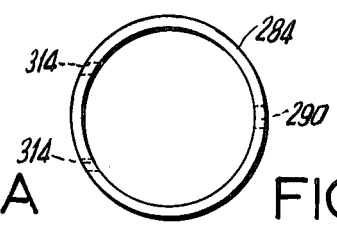
FIGS. 5A, 5B and 5C show end views of the sections of the coil assembly, in accordance with the present invention.
Figure 4B:
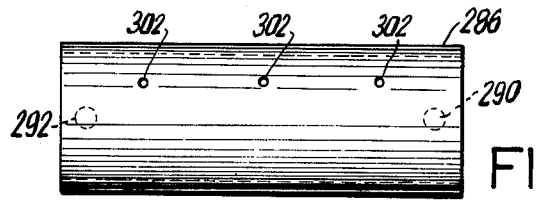
Figure 5B:
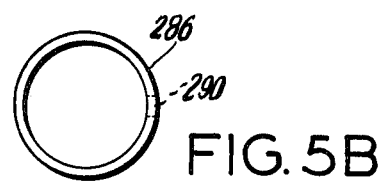
Figure 4C:
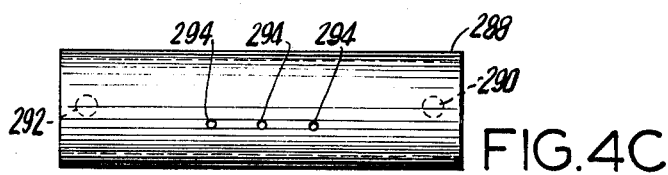
Figure 5C:
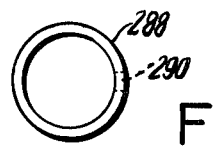

The operation of the circuit shown in FIG. 3 is as follows. The indifferent plate 134 is placed in contact with the patient and the unit is placed in its standby position. The standby switch 256 is moved upward and the operation switch 224 is moved downward. The standby bulb 242 will be illuminated and reduced standby voltage will be applied to the filaments of the vacuum tubes of the oscillator.

When the unit is to be operated, the standby switch 256 is placed in its lower position and the operating switch 224 is placed in its upward position, thereby providing the full filament voltage and producing the full +V voltage. Moving switch 224 upward also connects the high voltage to the output coil. To operate the forceps 106, the arms 108 and 110 are clamped onto a bleeding vessel. Continuing pressure on the forceps automatically closes the switch 118 thereby energizing the coil 124 by completing its circuit to ground 116. Coupled to the coil 124 are switches 96, 98 and 142. Switches 96 and 98 move to their b position which sends current passing through the arms of the forceps 108, 110. This current passes through the capacitors 281, 287 which allow actual shorting of the forceps together without stopping the system.

Switch 142 is moved onto position 140 which is now grounded through the switch to point 144. Grounding of this point turns on the transistors 278 which causes the coil 280 to become energized. This coil causes the switch 274 to move on its lower position thereby turning on the light emitting diode 270 indicating that the coagulation procedure is being utilized. Switch 230 also moves to its lower position j which cuts out the variac control 228 and provides the maximum output voltage from the transformer 214.

When switch 142 operates to ground position 140, it also turns on the multivibrator 170 and permits pulse modulation control of the oscillator through the amplifier switch 194. By adjusting the coagulation level control switch 192, the system can produce high peak power with a low average power by virtue of its operation at a short duty cycle. The coagulation level control is set at the desired power level required for coagulation procedures on a given patient.

Upon release of the arms 108 and 110, the coils 124 and 280 are both deenergized and all of the switches return back to their initial positions. In these initial positions, switches 96 and 98 are connected to their a point, which activates the cutter handpiece 102 and provides for a cutting procedure. However, the cutter handpiece will not be supplied with current until the switch 136 is actually placed onto its cut position. In so doing, point 146 is then grounded which turns on the amplifier switch 194 to keep the oscillator operating constantly. At the same time, with the relay 280 deactivated, the switch 274 activates the diode 268 providing a visual indication that a cutting output is being supplied. Switch 230 will also be in position i thereby including the variac control By manipulating the arm 228 on the variac control, the output voltage provided to the oscillator can be varied thereby controlling the intensity for the cutting procedure.

The cutter probe can also be used for coagulation purposes by operating switch 136 to its coagulation position, thereby grounding point 140. This serves to turn on the multivibrator and at the same time energize the relay 280 which cuts out the intensity control circuit and switches the indicating circuit to provide visual indication that the coagulation procedure is being utilized. The foot pedal 150 can operate in identical manner to the switch 136 and produce the same results.

It is noted from FIG. 3 that the indifferent plate 134 is not grounded, and the output is taken directly across the opposite ends of the output coil 92. The output is highly isolated from ground because the output voltage and current appears only across the two ends of the output coil rather than from either end to ground. In addition, the high degree of isolation is achieved by utilizing a unique design for the transformer coils which provides a completely balanced coil with a minimum of capacitive effect between the coils.

Referring now to FIGS. 4 through 8 there will be described the unique arrangement of the coil assembly. The coil assembly includes three sections of tubing 284, 286 and 288 which are each of cylindrical shape and precisely the same length. All three tubes contain alignment mounting holes 290 and 292 on opposite ends thereof. The largest tube 284 is used for winding of the output coil; the middle tube 286 is utilized for winding of the plate coil, and the smallest tube 288 is utilized for winding of the grid coil. Tube 288 contains three holes herein 294, through which the wires 296, 298 and 300 can pass, interconnecting to the point G, G', and Gc. The winding area for the tube 288 is precisely centered between the outermost holes.

The inner tube 286 also contains three holes 302, which permit the passage therein of the three wires 304, 306 and 308 respectively connecting to the end points P and P' and the mid point Pc. The winding area is precisely centered between the two outermost holes.

Figure 6:
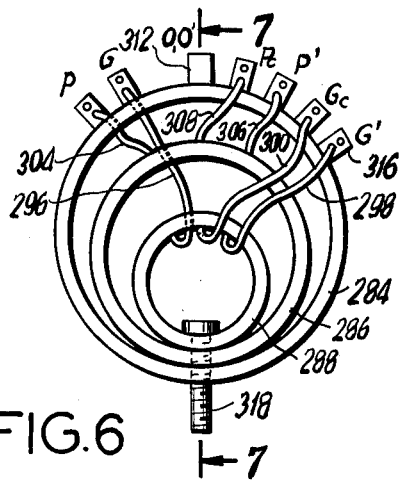
FIG. 6 shows an end view of the assembled coils, in accordance with the present invention.
Figure 7:
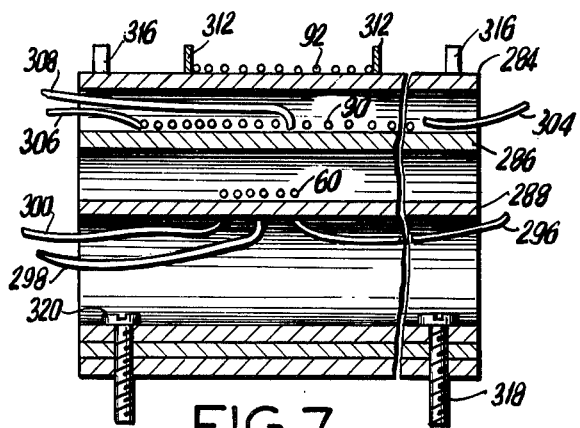
FIG. 7 shows a sectional view taken along line 7—7 of FIG. 6.
Figure 8:
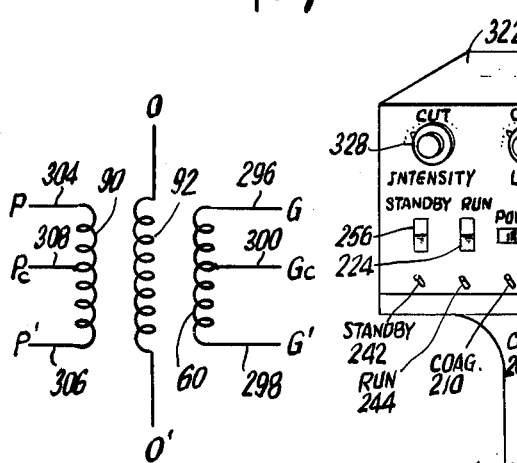
FIG. 8 shows a schematic circuit drawing of the transformer coil, in accordance with the present invention.

The upper most tube 284 contains two openings 310 through which terminals 312 can protrude, for connection thereto of the opposite ends of the coil 0 and 0'. Eyelet holes 314 are located in the outer edges of the tube 284 to permit the eyelet termnals 316 to pass therein and to which are connected the wires from the plate coil and the grid coil, as shown in FIG. 6.

The three coils are nested together and are assembled by means of the mounting screws 318 and 320 which respectively extend through the mounting holes 290 and 292. By utilizing the arrangement as shown, the winding can be located on precise centers of the three tubes without causing any unbalance between the tubes, thereby eliminating any capacitive effect between them. Although there may exist very small capacitive effects between the tubes and ground, such minute capacitive effects can be neglected because of their exceedingly small values. Additionally, by operating at a relatively low frequency, these capacitive effects are further diminished. Also, the coil can be isolated from the rest of the system to thereby additionally prevent the effects of such capacitive leakage paths to ground. Isolation is further enhanced by confining the output pickup coil to the center region of the plate coil so that coupling is predominantly magnetic with a minimum of capacitive coupling from the ends of the plate coil.

By way of example, the tubing can be made of high pressure laminated material. The length of each tubing can be approximately $3\frac{3}{8}$ inches with the winding area of the output coil being approximately one inch, the winding area of the plate coil being approximately $2\frac{1}{8}$ inches, and the winding area of the grid coil being approximately $\frac{3}{4}$ inch. The output coil would have approximately 20 coil turns with a 20 turns per inch winding density; the plate coil would have 76 coil turns with a density winding of 36 turns per inch, and the grid coil would have 34 coil turns with a winding density of 45 turns per inch. The outside diameter of the largest tube would be $1\frac{1}{8}$ inches; the outside diameter of the center tube would be $\frac{7}{8}$ inches and the outside diameter of the innermost tube would be 11/16 inches.

Utilizing such arrangement described and with a high output voltage of approximately 530 volts, there can be achieved a peak to peak voltage across the ends of the output coil of 1500 volts. Since the impedance ratio is the inverse of the turns ratio squared, there results a very low source impedance which provides a constant output power regardless of the loading on the system. Typically, the oscillator produces a frequency of 800 Kcs and the multivibrator produces a modulation frequency of 1 Kc. Utilizing the standby current to heat the filament of the tubes provides a warm-up time after the system is put in its run position of approximately 5-6 seconds to achieve full power. The low voltage applied to the control circuitry can typically be +8 volts.

Figure 10:
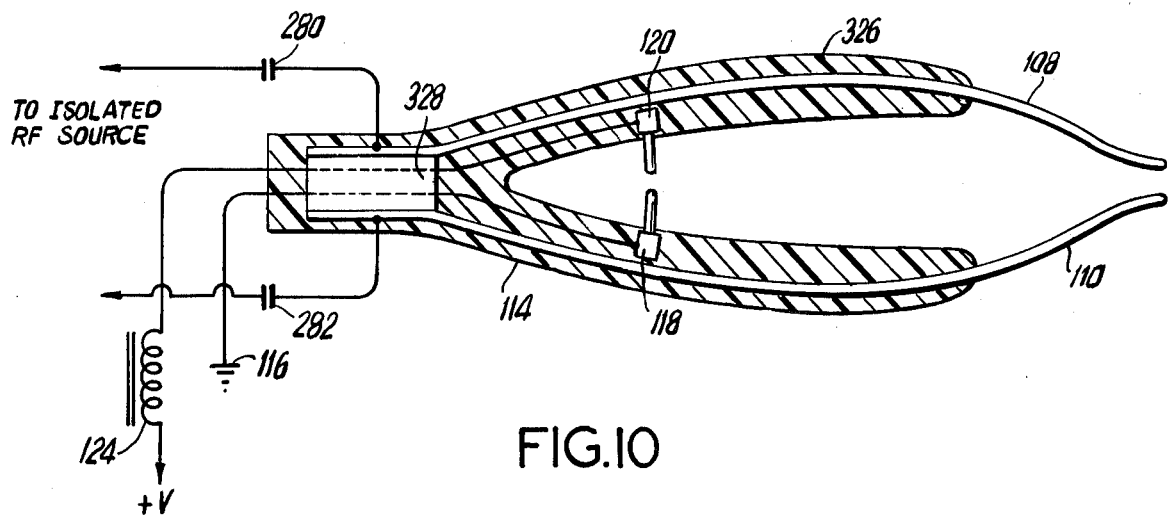
FIG. 10 shows a schematic drawing of an embodiment of the forceps for use in a coagulation procedure.
Figure 9:
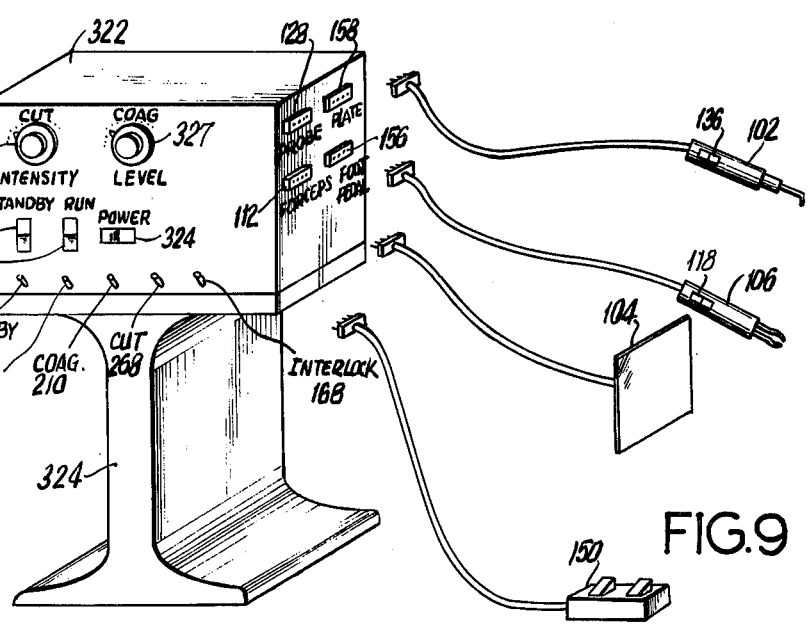
FIG. 9 shows an isometric view of the electrosurgical unit in accordance with the present invention.

Referring now to FIG. 9 it will be noted that the main body of the electrosurgical unit can be placed in a housing 322 which can be supported on a stand 324. The external equipment can be interconnected to the main unit by means of the plug and jack arrangements. The handpiece unit 102 can be interconnected to the jack 128; the forceps unit 106 can be interconnected to the jack 112; the indifferent plate unit 104 can be interconnected to the jack 158, and the foot pedal unit 150 can be interconnected to the jack 156. The switch 118 is shown locatd directly on the forceps. However, it can be inherently included within the arms of the forceps so that as the arms are brought together the switch is automatically closed, as is shown in FIG. 10. In this embodiment, the arms 108 and 110 are bowed outwardly with the switch contacts 118 and 120 positioned on the inner sides of the arms. As the arms 108 and 110 are brought together, the switches 118 and 120 contact each other to complete the circuit and energize the relay coil 124. The coagulation current is sent to the arms 108 and 110 through the capacitors 280 and 282. The arms 108 and 110 are insulated by the polyvinyl chloride encapsulation 326. The arms are also separated by the insulation block 328.

The switch 136 is shown located on the handpiece unit, however, it is also possible to include this switch directly on the main housing unit 322. The main housing unit includes the standby switch 256, the operating switch 224 and a main power switch which can be connected in series with the main source of energy. A dial switch 327 is connected to give an indication of the coagulation level and would be coupled to the variable control 192 of the multivibrator. A further dial 328 is provided to give an indication of the control of the variac arm 228 which controls the cut intensity. Five indicating bulbs are provided: the standby bulb 242, the operating bulb 244, the coagulation indicator 270, the cutting indicator 268, and the interlock warning indicator 168.

With the foregoing described arrangement it will be noted that the present invention provides an improved electrosurgical unit with a highly isolated output by using two vacuum tubes in push-pull arrangement for generating the RF signal. Furthermore, the isolation is achieved by utilizing low capacitance output cable and a uniquely arranged coil assembly which is completely balanced end to end. The output voltage and current appears only across the two ends of the output coil without having any part thereof grounded. Separate circuits are provided to control the output intensity of the cutting signal, by utilizing a variac in parallel with the main power supply transformer, and a separate control is provided for the coagulation intensity by controlling the duty cycle of the multivibrator which in turn pulse modulates the operation of the oscillator. While both a forceps for coagulation and a handpiece for cutting are provided, the cutting handpiece can also be utilized for coagulation. However, when either the forceps or the cutting probe are utilized, the other is prevented from being operational thereby preventing the possibility of causing burns to someone who may accidentally grab the unused instrument. An interlock is provided to warn when the indifferent plate has been disconnected. Additionally, upon disconnection of the indifferent plate, no current will be provided to the cutting handpiece. While a very high voltage is provided for the cutting and coagulating procedures, a low voltage is also provided for operating the transistors and the switches thereby avoiding the possibility of causing an explosion due to sparking at the switches. A standby low voltage filament supply is also included to provide for standby heating of the filament thereby reducing the warmup time when the system is turned on. Also, a preventive circuit is included to avoid the possiblity of having both the standby and the operating switches both being operated. Furthermore, the forceps are made such that they can be shorted together without necessarily disconnecting the operation of the entire system.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. An electrosurgical unit comprising:
   vacuum tube oscillator means for providing an ungrounded output of a given frequency;
   power supply means including a transformer for supplying said oscillator means with a high voltage;
   coagulation output means for coupling to said oscillator means, and providing a coagulation signal for use in coagulation procedures;
   cutting output means for coupling to said oscillator means, and providing a cutting signal for use in cutting procedures;
   switching circuit means for selectively connecting said coagulation output means or said cutting output means to said oscillator means;
   intensity control means for coupling to said power supply means, and varying the voltage supplied to said oscillator means, said intensity control means including a variable coil in parallel with said transformer for controlling the output voltage across said transformer;
   modulation means for coupling to said oscillator means, and providing intermittent operation of said oscillator means, said modulation means including a multivibrator means, and coagulation level control means for varying the duty cycle of said multivibrator means;
   and operation control means in said switching circuit means for interconnecting said intensity control means to said power supply means when said cutting output means is connected to said oscillator means, for interconnecting said modulation means to said oscillator means when said coagulation output means is connected to said oscillator means, and for disconnecting from said oscillator means one of said modulation means or said intensity control means when the other is connected thereto.

2. An electrosurgical unit as in claim 1, and wherein said cutting output means comprises a handpiece unit for applying said cutting signal as a high current density RF signal, and a return plate for returning the signal to said oscillator means, and wherein both said handpiece unit and said return plate are isolated from ground.

3. An electrosurgical unit as in claim 1, and wherein said oscillator means comprises first and second vacuum tubes coupled in push-pull arrangement, and a balanced three coil transformer unit, including a first coil having its ends respectively connected to the grids of said vacuum tubes and its mid point coupled to ground, a second coil having its ends respectively connected to the plates of said vacuum tube and its mid point coupled to said power supply means, and a third output coil having its ends coupled through said switching circuit means to said coagulation output means and said cutting output means.

4. An electrosurgical unit as in claim 3 and wherein said transformer unit comprises three cylindrical tubes of equal length and of sequentially increasing diameter size, all containing aligned mounting holes at the ends thereof, said three tubes being mounted together through the holes, said three coils being wound respectively on said three tubes, the center portion of each tube being utilized as the winding area to completely balance the windings on each side of the center, thereby removing any capacitive effects between the tubes.

5. An electrosurgical unit as in claim 4 and further comprising mounting screws, and wherein said tubes are coupled together by said mounting screws cooperating with said mounting holes maintaining said cylindrical tubes in a tangentially interconnected arrangement.

6. An electrosurgical unit as in claim 3, and wherein the number of turns in said third coil is substantially less than the number of turns in said second coil and positioned centrally thereof, thereby providing a high voltage across the output, a low source impedance, and reducing capacitive coupling between said second and third coils.

7. An electrosurgical unit as in claim 1, and wherein said switching circuit means including said operation control means comprises a first switch interconnecting said oscillator means to a first and second position, said cutting output means being connected to said first position and said coagulation output means being connected to said second position, a second switch having a first position interconnecting said intensity control means to said power supply means and a second position disconnecting said intensity control means from said power supply means, a third switch having a first position disconnecting said modulation means from said oscillator means and a second position connecting said modulation means to said oscillator means, said first, second and third switches normally being in their respective first positions, a first relay coil means for switching said first and third switches into their respective second positions upon energization thereof, control switch means energizing said first relay coil means when in a closed position, and a second relay coil means energized by the closing of said third switch for switching said second switch into its respective second position.

8. An electrosurgical unit as in claim 7, and wherein said coagulation output means includes forceps means connected across said osciallator means output, said control switch means being coupled to said forceps means.

9. An elctrosurgical unit as in claim 7, and wherein said cutting output means includes handpiece means and an operating switch thereon, said operating switch having a cutting position and a coagulation position, said operating switch connected in parallel with said third switch, whereby said cutting position corresponds to the first position of said third switch and said coagulation position corresponds to the second position of said third switch, and wherein said cutting oiutput means can be utilized to selectively provide said cutting signal as well as said coagulation signal to said handpiece means.

10. An electrosurgical unit as in claim 9, and further comprising a foot pedal switch connected in parallel with said operating switch.

11. An electrosurgical unit as in claim 7, and further comprising cutting indicator means and coagulation indicator means, and wherein said switching circuit means further comprises a fourth switch having a first position connecting to said cutting indicator means and a second position connected to said coagulation indicator means, said fourth switch operating in conjunction with said second switch.

12. An electrosurgical unit as in claim 1 and wherein said oscillator means includes vacuum tubes having filaments and wherein said power supply means comprises a high voltage output circuit means for connection to the output of said oscillator means, a low voltage output circuit means for connection to said switching means, and a filament voltage circuit means coupled to the filaments of said vacuum tubes.

13. An electrosurgical unit as in claim 1, and wherein said filament voltage circuit means includes an operating voltage level output and a standby voltage level output less than said operating voltage level output, and further comprising a standby switch and an operating switch connected to aid power supply means, said standby switch selecting said standby voltage level output and said operating switch selecting said operating voltage level output, said operating switch also interconnecting said high voltage output circuit means to said oscillator means.

14. An electrosurgical unit as in claim 13, and further comprising circuit protection means for preventing the simultaneous operation of both said standby switch and said operating switch.

15. An electrosurgical unit as in claim 13, and further comprising standby indicator means and operating indicator means for respectively indicating which of said standby switch and said operating switch has been activated.

16. An electrosurgical unit as in claim 1, and wherein said coagulation output means includes a forceps having spaced apart ends across which said coagulation signal is provided, and wherein said cutting output means includes handpiece means and a return plate across which said cutting signal is provided, said forceps including an integral switch in the arms of the forceps which closes when the forceps arms are brought together.

17. An electrosurgical unit as in claim 16, and wherein said cutting output means further includes a control switch means for permitting said cutting output means to selectively provide said cutting signal as well as said coagulation signal.

18. An electrosurgical unit as in claim 16, and wherein said return plate includes interlock means for providing an indication when said return plate is physically detached from said oscillator means.

19. An electrosurgical unit as in claim 16, and wherein said coagulation output means further comprises two wires respectively connected to said spaced apart ends and capable of interconnecting to said oscillator means, and capacitor means respectively interconnected in each of said two wires.

20. An electrosurgical unit as in claim 16, and further comprising housing means containing thereon a first plug means connected in said coagulation output means for connecting thereto said forceps, a second plug means connected in said cutting output means for connecting thereto said handpiece means, a third plug means connected in said cutting output means for connecting thereto said return plate, a first switch means connected in said power supply means for activating said power supply means in a standby condition, a second switch means connected in said power supply means for activating said power supply means in an operating condition, a first dial means for operating said variable coil and a second dial means for operating said coagulation level control means.

21. An electrosurgical unit as in claim 20, and further comprising a foot control unit, and wherein said housing means further contains thereon a fourth plug connected in said switching circuit means for connecting thereto said foot control unit.

22. An electrosurgical unit as in claim 20, and further comprising first indicator means providing an indication when said unit is in a standby condition, second indicator means for indicating when said unit is in an operating condition, third indicator means indicating when said coagulation output is being supplied, fourth indicator means for indicating when said cutting output is being supplied and interlock warning indicator means for indicating when said return plate has been disconnected from said housing means.

* * * * *